US012765751B2

(12) United States Patent
Norling

(10) Patent No.: US 12,765,751 B2
(45) Date of Patent: Oct. 20, 2026

(54) FIBER OPTIC SENSOR RETRACTION SYSTEM

(71) Applicant: Acies Medical LLC, Saint Paul, MN (US)

(72) Inventor: Brian L. Norling, Santa Barbara, CA (US)

(73) Assignee: Acies Medical LLC, Saint Paul, MN (US)

( * ) Notice: Subject to any disclaimer, the term of this patent is extended or adjusted under 35 U.S.C. 154(b) by 434 days.

(21) Appl. No.: 18/559,489

(22) PCT Filed: May 20, 2022

(86) PCT No.: PCT/US2022/030270
§ 371 (c)(1),
(2) Date: Nov. 7, 2023

(87) PCT Pub. No.: WO2022/246208
PCT Pub. Date: Nov. 24, 2022

(65) Prior Publication Data

US 2024/0237884 A1 Jul. 18, 2024

Related U.S. Application Data

(60) Provisional application No. 63/191,627, filed on May 21, 2021.

(51) Int. Cl.
*A61B 1/00* (2006.01)
*A61B 1/015* (2006.01)
(Continued)

(52) U.S. Cl.
CPC ...... *A61B 1/00154* (2013.01); *A61B 1/00016* (2013.01); *A61B 1/00165* (2013.01);
(Continued)

(58) Field of Classification Search
CPC ........... A61B 1/00154; A61B 1/00016; A61B 1/00165; A61B 1/015; A61B 1/046;
(Continued)

(56) References Cited

U.S. PATENT DOCUMENTS 4,435,037 A 3/1984 Abramson et al.
4,564,011 A 1/1986 Goldman
(Continued)

FOREIGN PATENT DOCUMENTS

CN 201361376 Y 12/2009
CN 101710074 A 5/2010
(Continued)

OTHER PUBLICATIONS

Office Action pertaining to U.S. Appl. No. 17/296,020, mailed Jun. 21, 2024.
(Continued)

*Primary Examiner* — Tasnim Mehjabin Ahmed
(74) *Attorney, Agent, or Firm* — GRUMBLES LAW PLLC; Bryan Kravis

(57) ABSTRACT

A fiber optic sensor retraction system comprising a hollow needle for administering medical fluids located at a distal end of the retraction system, a proximal end of the retraction system that includes an opening configured to receive medical fluids through a fluid channel, and a spring housing connected between the distal and proximal ends of the retraction system. The fiber optical system comprises a fiber optic waveguide that is at least partially contained within the hollow needle and extending through a Y-junction for detecting and light from a biomarker luminescent material at a distal end of the hollow needle. The fiber optic sensor retraction system further contains a syringe containing medi-
(Continued)

cal fluids in fluid communication with the Y-junction. A spring in mechanical communication with the fiber optic waveguide.

17 Claims, 3 Drawing Sheets

(51) Int. Cl.

| | |
|---|---|
| ***A61M 5/158*** | (2006.01) |
| *A61B 1/04* | (2006.01) |
| *A61M 25/00* | (2006.01) |
| *A61M 25/06* | (2006.01) |
| *G01N 21/76* | (2006.01) |
| *G01N 21/77* | (2006.01) |

(52) U.S. Cl.

CPC ............. *A61B 1/015* (2013.01); *A61M 5/158* (2013.01); *A61B 1/043* (2013.01); *A61M 2005/1583* (2013.01); *A61M 2005/1587* (2013.01); *A61M 2005/1588* (2013.01); *A61M 2025/0091* (2013.01); *A61M 25/065* (2013.01); *G01N 21/76* (2013.01); *G01N 2021/7786* (2013.01)

(58) Field of Classification Search

CPC ..... A61B 1/043; A61M 5/158; A61M 25/065; A61M 2005/1583; A61M 2005/1587; A61M 2005/1588

See application file for complete search history.

(56) References Cited

U.S. PATENT DOCUMENTS

| | | | |
|---|---|---|---|
| 4,588,256 | A | 5/1986 | Onstott et al. |
| 4,589,404 | A | 5/1986 | Barath et al. |
| 4,681,398 | A | 7/1987 | Bailey et al. |
| 4,682,848 | A | 7/1987 | Cairns et al. |
| 4,754,328 | A | 6/1988 | Barath et al. |
| 5,178,153 | A | 1/1993 | Einzig |
| 5,251,276 | A | 10/1993 | Berkey et al. |
| 5,312,374 | A | 5/1994 | Gurmarnik |
| 5,405,474 | A | 4/1995 | Berkey et al. |
| 5,460,182 | A | 10/1995 | Goodman et al. |
| 5,938,595 | A | 8/1999 | Glass et al. |
| 6,027,493 | A | 2/2000 | Donitzky et al. |
| 6,134,003 | A | 10/2000 | Tearney et al. |
| 6,231,568 | B1 | 5/2001 | Loeb et al. |
| 6,246,901 | B1 | 6/2001 | Benaron |
| 6,277,082 | B1 | 8/2001 | Gambale |
| 6,296,608 | B1 | 10/2001 | Daniels et al. |
| 6,325,883 | B1 | 12/2001 | Backer et al. |
| 6,331,178 | B1 | 12/2001 | Loeb et al. |
| 6,357,447 | B1 | 3/2002 | Swanson et al. |
| 6,423,296 | B1 | 7/2002 | Gunther et al. |
| 6,514,277 | B1 | 2/2003 | Lilge et al. |
| 6,551,302 | B1 | 4/2003 | Rosinko et al. |
| 6,554,794 | B1 | 4/2003 | Mueller et al. |
| 6,564,087 | B1 | 5/2003 | Pitris et al. |
| 6,993,376 | B2 | 1/2006 | Testardi |
| 7,022,109 | B1 | 4/2006 | Ditto |
| 7,189,226 | B2 | 3/2007 | Auld et al. |
| 7,524,316 | B2 | 4/2009 | Hennings et al. |
| 7,787,923 | B2 | 8/2010 | Alarcon et al. |
| 8,054,452 | B2 | 11/2011 | Bado et al. |
| 8,235,602 | B2 | 8/2012 | Rohlen |
| 8,269,953 | B2 | 9/2012 | Bado et al. |
| 8,694,069 | B1 | 4/2014 | Kosa et al. |
| 9,420,967 | B2 | 8/2016 | Zand et al. |
| 9,820,662 | B2 | 11/2017 | Weber et al. |
| 10,231,634 | B2 | 3/2019 | Zand et al. |
| 10,342,416 | B2 | 7/2019 | Bierhoff et al. |
| 10,342,575 | B2 | 7/2019 | Cox et al. |
| 10,342,993 | B2 | 7/2019 | Perkins et al. |
| 10,470,712 | B2 | 11/2019 | Sipple |
| 2001/0023346 | A1 | 9/2001 | Loeb |
| 2002/0037149 | A1 | 3/2002 | Chen |
| 2003/0045798 | A1 | 3/2003 | Hular et al. |
| 2003/0068827 | A1 | 4/2003 | Morris et al. |
| 2003/0114842 | A1 | 6/2003 | Distefano |
| 2003/0163016 | A1 | 8/2003 | Testardi |
| 2004/0010204 | A1 | 1/2004 | Weber et al. |
| 2004/0019280 | A1 | 1/2004 | Waner et al. |
| 2004/0086230 | A1 | 5/2004 | Lewandowski et al. |
| 2004/0175821 | A1 | 9/2004 | Ehman |
| 2005/0004453 | A1 | 1/2005 | Tearney et al. |
| 2005/0033389 | A1 | 2/2005 | Auld et al. |
| 2005/0113657 | A1 | 5/2005 | Alarcon et al. |
| 2006/0200121 | A1 | 9/2006 | Mowery |
| 2006/0235270 | A1 | 10/2006 | Teichmann |
| 2006/0241503 | A1 | 10/2006 | Schmitt et al. |
| 2007/0065481 | A1 | 3/2007 | Chudzik et al. |
| 2007/0148782 | A1 | 6/2007 | Pawliszyn |
| 2007/0255264 | A1 | 11/2007 | Hickingbotham |
| 2007/0270788 | A1 | 11/2007 | Nahen et al. |
| 2008/0009751 | A1 | 1/2008 | Berndt |
| 2008/0021527 | A1 | 1/2008 | Hennings et al. |
| 2008/0287916 | A1 | 11/2008 | Agmon |
| 2010/0241100 | A1* | 9/2010 | Blumenfeld ......... A61B 5/6849 600/584 |
| 2011/0092823 | A1 | 4/2011 | Tearney et al. |
| 2011/0136132 | A1 | 6/2011 | Tseng et al. |
| 2011/0152759 | A1 | 6/2011 | Clymer et al. |
| 2011/0164249 | A1 | 7/2011 | Innami et al. |
| 2011/0184350 | A1 | 7/2011 | Mckay |
| 2011/0306854 | A1 | 12/2011 | Arnold et al. |
| 2012/0065519 | A1 | 3/2012 | Mincu et al. |
| 2013/0345527 | A1 | 12/2013 | Ozdil et al. |
| 2014/0012186 | A1 | 1/2014 | Thyzel |
| 2014/0025000 | A1 | 1/2014 | Currie et al. |
| 2014/0378905 | A1 | 12/2014 | Senatore |
| 2015/0057530 | A1 | 2/2015 | Roggeveen et al. |
| 2016/0008057 | A1 | 1/2016 | Peppou |
| 2016/0310704 | A1 | 10/2016 | Ng et al. |
| 2017/0135561 | A1 | 5/2017 | Snoke et al. |
| 2017/0172507 | A1 | 6/2017 | Sipple |
| 2017/0173275 | A1 | 6/2017 | Anderson et al. |
| 2017/0231563 | A1* | 8/2017 | Tsamir ............... A61B 17/3496 604/512 |
| 2017/0311807 | A1 | 11/2017 | Fu et al. |
| 2018/0008172 | A1 | 1/2018 | Mycek et al. |
| 2018/0014764 | A1 | 1/2018 | Bechtel et al. |
| 2022/0015635 | A1 | 1/2022 | Sipple et al. |

FOREIGN PATENT DOCUMENTS

| | | | |
|---|---|---|---|
| CN | 102016552 | A | 4/2011 |
| CN | 102445444 | A | 5/2012 |
| CN | 206887114 | U | 1/2018 |
| CN | 108114347 | A | 6/2018 |
| CN | 109689127 | A | 4/2019 |
| DE | 102014107342 | A1 | 11/2015 |
| DE | 102016221065 | A1 | 4/2018 |
| EP | 1884211 | A2 | 2/2008 |
| JP | 2005501586 | A | 1/2005 |
| KR | 1020110033610 | B1 | 12/2011 |
| KR | 101293690 | B1 | 8/2013 |
| WO | 2013046993 | A1 | 4/2013 |
| WO | 2014120901 | A1 | 8/2014 |
| WO | 2015196172 | A2 | 12/2015 |
| WO | 2020106555 | A1 | 5/2020 |

OTHER PUBLICATIONS

Office Action pertaining to corresponding Chinese Patent Application No. 201980076899.6, mailed Aug. 31, 2024.

Indian Patent Application for corresponding Indian Application No. 202217022931, mailed Sep. 13, 2024.

Examination Report pertaining to Australian Patent Application No. 2019384705, mailed May 31, 2024.

Office Action pertaining to Chinese Patent Application No. 201980076899.6, mailed May 16, 2024.

(56) References Cited

OTHER PUBLICATIONS

Search Report pertaining to European Patent Application No. 20906030.0, mailed Dec. 8, 2023.
Philips Electronics Nederland Bv, Integrated Spectrometers for SpectralTissue Sensing, European Commision, Horizon 2020, https://cordis.europa.eu/project/id/644483/reporting, accessed Dec. 7, 2023.
Final Rejection pertaining to U.S. Appl. No. 17/296,020, mailed Oct. 1, 2024.
Office Action pertaining to corresponding Mexican Patent Application MX/a/2021/005947, issued Sep. 11, 2024.
Extended European Search Report pertaining to European Patent Application No. 20906030.0, mailed Feb. 29, 2024.
Office Action pertaining to U.S. Appl. No. 17/779,250, mailed Jun. 3, 2025.
Japanese Office Action pertaining to Japanese Patent Application No. 2022-535636, mailed May 14, 2024.
Restriction Requirement pertaining to corresponding U.S. Appl. No. 17/296,020, mailed Jan. 18, 2024.
Examination Report pertaining to Canadian Patent Application No. 3120510, dated Nov. 19, 2024.
Examination Report pertaining to European Patent Application No. 19887769.8, mailed Nov. 27, 2024.
Office Action pertaining to corresponding Chinese Patent Application No. 202080077177.5, mailed Dec. 13, 2024.
Advisory Action pertaining to corresponding U.S. Appl. No. 17/296,020, mailed Dec. 19, 2024.
Office Action pertaining to Chinese Patent Application No. 201980076899.6 mailed Jan. 9, 2024.
"Single Mode Fiber Distance, Diameter, Speed, Bandwidth Basis" published at FS.com on Sep. 8, 2012 (Year: 2012).
Examination Report pertaining to corresponding Indian Patent Application No. 202117026815, mailed Oct. 27, 2022.
Extended European Search Report pertaining to corresponding European Patent Application No. 15810409.1, dated Jan. 22, 2018.
International Search Report and Written Opinion for International Application No. PCT/US2015/036830, dated Sep. 23, 2015; date of filing: Jun. 19, 2015; 5 pages.
International Search Report and Written Opinion pertaining to PCT/US2019/061609, dated Feb. 18, 2020.
International Search Report and Written Opinion pertaining to PCT/US2020/063181, mailed Apr. 2, 2021.
International Search Report and Written Opinion pertaining to PCT/US2022/030270, mailed Aug. 16, 2022.
Office Action pertaining to corresponding Japanese Patent Application No. 2021-528859, mailed Mar. 28, 2023.
Balthasar et al., "Spectral Tissue Sensing to Identify intra- and extravascular needle placement—A randomized single-blind controlled trial", Mar. 9, 2017, PLOS One, pp. 1-13.
Russell et al., "Development of a needle shaped microelectrode for electrochemical detection of the sepsis biomarker interleukin-6 (IL-6) in real time", Biosensors and Bioelectronics, 2019, 126, 806-814.
Supplementary European Search Report pertaining to corresponding European Patent Application No. 19887769.8, mailed Jul. 19, 2022.
Supplementary Search Report and Search Opinion for European Application No. 15810409.1; dated Jan. 22, 2018; date of filing: Jun. 19, 2015; 6 pages.

* cited by examiner

FIBER OPTIC SENSOR RETRACTION SYSTEM

CROSS-REFERENCE TO RELATED APPLICATIONS

This application claims the benefit of U.S. provisional Application No. 63/191,627, filed May 21, 2021 and titled FIBER OPTIC SENSOR RETRACTION SYSTEM.

The aforementioned patent applications are hereby incorporated by reference, such incorporation being limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

FIELD OF THE DISCLOSURE

The present disclosure relates to a fiber optic sensor retraction system useful for extracting a fiber optic waveguide from a hollow bore needle in medical procedures.

BACKGROUND

Efforts to improve surgical outcomes and cost structure, particularly with spinal surgery or dental procedures, have led to increased use of minimally invasive procedures. These procedures often use image-guided modalities such as fluoroscopy, CT, nerve stimulators, and, more recently, the Doppler ultrasound test. While often involving less risk than surgery, minimally invasive spinal procedures, pain management procedures, nerve blocks, ultrasound guided interventions, biopsy, and percutaneous placement or open intraoperative placement continue to carry risks of ineffective outcome and iatrogenic injuries, such as infection, stroke, paralysis and death due to penetration of various structures including, but not limited to, organs, soft tissues, vascular structures, and neural tissue such as, catastrophically, the spinal cord. Injuries can occur regardless of practitioner experience because a surgical instrument must proceed through several layers of bodily tissues and fluids to reach the desired space in the spinal canal.

To illustrate, the intrathecal (or subarachnoid) space of the spinal region, where many medications are administered, houses nerve roots and cerebrospinal fluid (CSF) and lays between two of the three membranes that envelope the central nervous system. The outermost membrane of the central nervous system is the dura mater, the second is the arachnoid mater, and the third, and innermost membrane, is the pia mater. The intrathecal space is in between the arachnoid mater and the pia mater. To get to this area, a surgical instrument may need to first get through skin layers, fat layers, the interspinal ligament, the ligamentum flavum, the epidural space, the dura mater, the subdural space, and the intrathecal space. Additionally, in the case of a needle used to administer medication, the entire needle opening must be within the sub-arachnoid space.

Because of the complexities involved in inserting a surgical instrument into the intrathecal space, penetration of the spinal cord and neural tissue is a known complication of minimally invasive spine procedures and spine surgery. Additionally, some procedures require the use of larger surgical instruments. For example, spinal cord stimulation, a form of minimally invasive spinal procedure wherein small wire leads can be inserted in the spinal epidural space, may require that a 14-gauge needle be introduced into the epidural space in order to thread the stimulator lead. Needles of this gauge are technically more difficult to control, posing a higher risk of morbidity. Complications can include dural tear, spinal fluid leak, epidural vein rupture with subsequent hematoma, and direct penetration of the spinal cord or nerves with resultant paralysis. These and other high-risk situations, such as spinal interventions and radiofrequency ablation, can occur when a practitioner is unable to detect placement of the needle or surgical apparatus tip in critical anatomic structures.

At present, detection of such structures is operator dependent, wherein operators utilize tactile feel, contrast agents, anatomical landmark palpation and visualization under image-guided modalities. The safety of patients can rely upon the training and experience of the practitioner in tactile feel and interpretation of the imagery. Even though additional training and experience may help a practitioner, iatrogenic injury can occur independently of practitioner experience and skill because of anatomic variability, which can arise naturally or from repeat procedures in the form of scar tissue. Fellowship training in some procedures, such as radiofrequency ablation, may not be sufficiently rigorous to ensure competence; even with training, outcomes from the procedure can vary considerably. In the case of epidural injections and spinal surgery, variability in the thickness of the ligamentum flavum, width of the epidural space, dural ectasia, epidural lipomatosis, dural septum, and scar tissue all can add challenges to traditional verification methods even for highly experienced operators. Additionally, repeat radiofrequency procedures done when nerves regenerate, often a year or more later, are often less effective and more difficult because the nerves' distribution after regeneration creates additional anatomic variability.

SUMMARY OF THE INVENTION

A fiber optic sensor retraction system is disclosed that provides a methodology for a mechanism for rapidly extracting a fiber optic waveguide sensor from the interior of a hollow needle when the needle is properly placed in a medical or surgical procedure.

In one aspect, a retraction system for a fiber optic sensor is disclosed. The retraction system includes a hollow needle, such as a hypodermic needle, for administering medical fluids. The hollow needle can be in fluid communication with a y-junction. The y-junction can have a first input arm, a second input arm, and an output arm. The fiber optic sensor (waveguide) may be in one embodiment at least partially contained within the hollow needle and extend through the y-junction into the first input arm of the y-junction. A syringe can include a medical fluid in fluid communication with the second input arm of the y-junction. The disclosed retraction system can also include a retraction spring within the first input arm that is in mechanical communication with the fiber optic sensor. In some embodiments, the disclosed retraction system also includes a trigger in mechanical communication with the retraction spring.

More specifically, the fiber optic sensor retraction system may include a distal end, a proximal end, a hollow needle located at the distal end of the retraction system, an opening at the proximal end of the retraction system, a spring housing connected between the distal and proximal ends of the retraction system, an optical system comprising a fiber optic waveguide, a syringe containing medical fluids, and a spring that is in mechanical communication with the fiber optic waveguide. The opening can be configured to receive medical fluids through a fluid channel. The fiber optic waveguide can be at least partially contained within the hollow needle, can extend through a Y-junction, and can be configured to detect light from a biomarker luminescent material at a distal end of the hollow needle. The syringe can be in fluid communication with the Y-junction.

In some cases, the spring can be a retraction spring, the hollow needle can be in fluid communication with the Y-junction, and the fluid channel can be comprised of a first input arm, a second input arm, and an output arm, wherein the spring is connected to the first input arm. Further, the fiber optic waveguide can be located within a lumen of the fluid channel and can be further comprised of at least an optical fiber, an optical coupler, or both.

In some cases, the fiber optic sensor retraction system is further comprised of a retraction trigger in mechanical communication with the spring. The fiber optic sensor retraction system may be comprised of a notification system in communications with the optical system that informs a clinician that a target biomarker has been detected. The fiber optic sensor retraction system may be comprised of the medicinal fluid that is delivered through the fluid channel in the syringe to a biological system.

In some cases, the optical system can deliver light to biomarker luminescent material and simultaneously transmit emitted light from the biomarker luminescent material to a detector in the optical system. And in some cases, the proximal end can comprise a luer lock that is configured to receive the syringe. In some cases, the optical system further comprises an optical receiver having a filter that can selectively prevent frequencies other than the frequency of emitted light from the biomarker luminescent material from reaching the optical receiver. The optical system may be configured to send optical signals from the needle through the fiber optic waveguide. The optical fiber can be located within a lumen of the output arm and can be retracted allowing medicinal fluid to flow through the fluid channel and into a biological system.

In some cases, the spring can be at least one of a helical coil, solenoid based, disc, Belleville washer, wave spring or any combination thereof. A spring recoil rate may be preselected based on a spring tension. The spring housing can be configured to house the spring and at least a portion of the optical fiber. The retraction spring can be held retracted by a pin.

And in some cases, the proximal end of the retraction system can contain a luer lock configured to connect with the syringe. The fiber optic sensor retraction system can be further comprised of a barrel connected to the optical fiber, wherein the optical fiber can have a smaller diameter than the barrel. In some cases, the fiber optic sensor retraction system can be further comprised of a detector having a circuit board that includes one or more wireless interfaces.

In another aspect, a fiber optic fluid delivery device is disclosed, wherein the device is comprised of a fluidic delivery system comprising a delivery device, the delivery device having a distal end, and a detection system in communication with a target biomarker. The fluidic delivery system can be configured to detect the target biomarker in a biological system, the fluidic delivery system can be in contact with the target biomarker, and the delivery device can include a lumen and a fluid channel. The detection system can detect bioluminescent light for determining the presence of the target biomarker.

In another aspect, a method for retracting a fiber optic sensor is disclosed that includes providing a fiber optic sensor retraction system according to the disclosure above. The method further includes inserting the needle containing the fiber optic wavelength sensor into a patient and using the fiber optic wavelength sensor to properly place the needle. The method includes retracting the fiber optic wavelength sensor and then administering medical fluids through the hollow needle.

DETAILED DESCRIPTION

Figure 1:
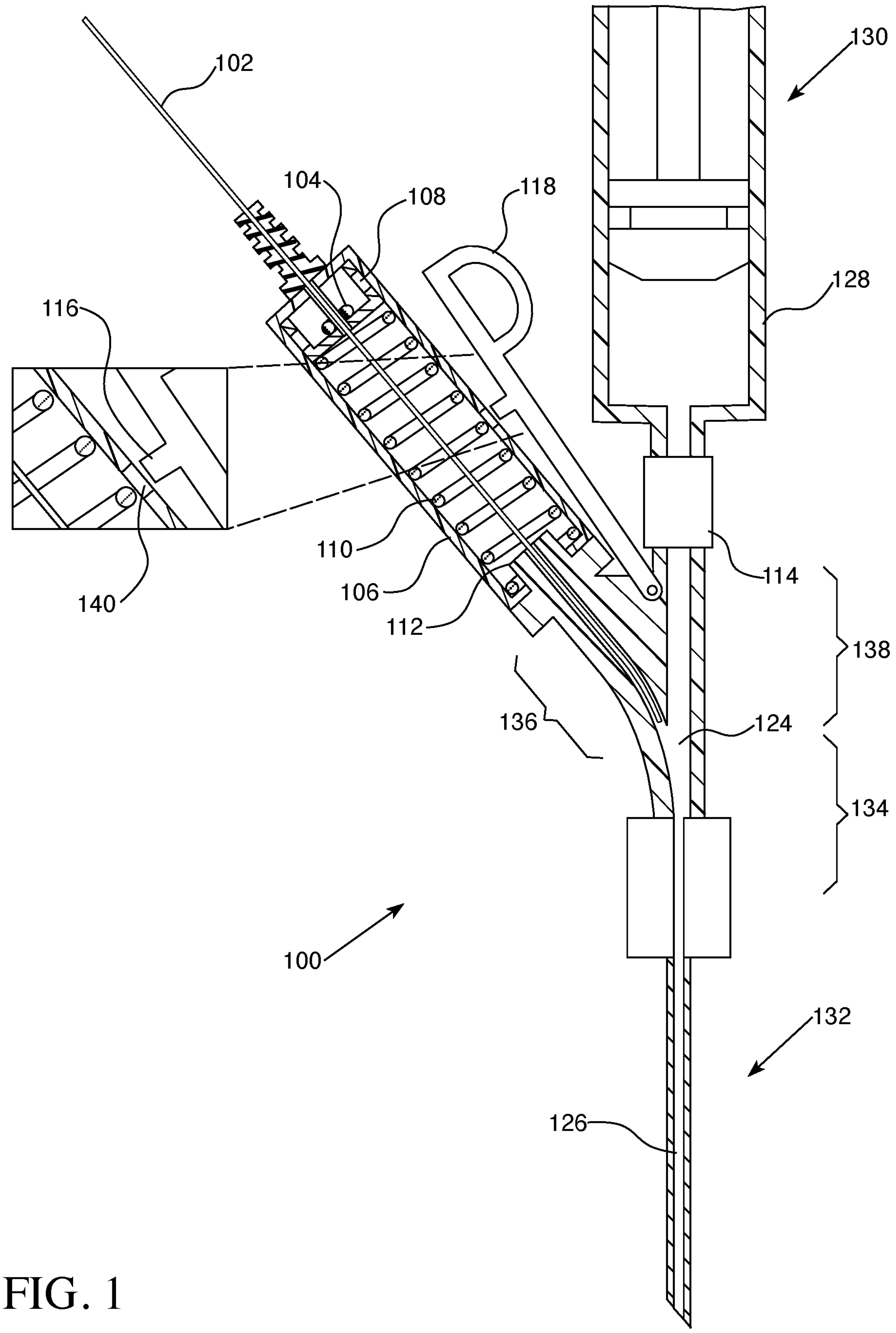
FIG. 1 is an illustrative example of an embodiment of a fiber optic retraction system according to the present disclosure.

The present disclosure relates to fiber optic sensor retraction systems and methods used to detect biological substances, such as bodily fluids and tissues, including blood. Various embodiments of fiber optic sensor retraction systems and methods are be described in detail with reference to the drawings, wherein like reference numerals may represent like parts and assemblies throughout the several views. Reference to various embodiments does not limit the scope of the fiber optic sensor retraction system disclosed herein. Additionally, any examples set forth in this specification are not intended to be limiting and merely set forth some of the many possible embodiments for the fiber optic sensor retraction system. It is understood that various omissions and substitutions of equivalents are contemplated as circumstances may suggest or render expedient, but these are intended to cover applications or embodiments without departing from the spirit or scope of the disclosure. Also, it is to be understood that the phraseology and terminology used herein are for the purpose of description and should not be regarded as limiting.

Fiber optic waveguides can be placed in the interior of hollow needles useful in medical procedures. The proper placement of the needles can be critical in the success of medical procedures such as surgical procedures on the nervous system (i.e. spinal surgery) or dental procedures. The fiber optic waveguide can be used as part of a sensor system that can detect important biological structures. For example, when trying to inject an anesthetic into a patient in a dental setting, it can be desirable to avoid injecting the medication into a blood vessel which can cause negative undesirable systemic reactions in a patient. A fiber optic sensor in the injection needle can be a part of a detection system that detects iron ions (in blood, for example) and can indicate the improper placement of the needle. In this case the needle can be relocated so that the anesthetic is properly injected. In some embodiments, the sensor may be located level with the needle tip or bevel. This location may allow the sensor to detect blood or other biomarkers at or near the tip of the needle.

In another example, spinal surgeons may want to locate various biological structures when placing a needle for administration of a medicament. In these cases, the surgeon may wish to find spinal fluid or avoid other physiological structures. A fiber optic detector can be placed into the needle which can be part of a detection system that can identify biological tissues in contact with the needle opening.

In normal operation, the surface of the fiber optic waveguide sensor within a hollow needle can be roughly coplanar with the tip of the Quincke needle. The fiber optic waveguide can be much smaller than the needle bore, allowing for injection of fluids, such as medicaments, to flow past the fiber optic waveguide. In some modalities, the entire needle bore can be filled with the fiber optic waveguide. In these cases, it can be necessary to retract or remove the fiber optic waveguide prior to the injection of fluids.

The removal of fiber optic waveguides can be done by hand by pulling the optical fiber waveguide into a Y-junction of guided syringe placement and delivery system until the fiber optic waveguide clears the needle bore. Hand removal of the optical fiber waveguide can be a significant operation by the surgeon or surgical staff at the precise point of injection, when movement of the needle tip is undesirable. Such a manual procedure also can require extra time for the whole procedure. Additionally, if a hard stop for fiber retraction is not included in the delivery system, it is possible for a leak to be created. However, this is unlikely based upon the approach of using a flexible polymer membrane similar to that used on a sealed medicine bottle or vial.

The present disclosure is to a novel fiber optic waveguide sensor retraction system and method to enable rapid extraction of the fiber optic waveguide when needle placement is finalized. The objective is to extract the fiber rapidly with a minimal action by the surgeon or surgical staff member and with minimal or negligible movement of the needle tip.

In the simplest embodiment disclosed herein, a spring is employed with a trigger release to rapidly extract the fiber. This embodiment is illustrated in FIG. 1 and may incorporate a spring for stored motive force. As shown, a trigger for release of the spring is provided as well as a polymer seal system to maintain sterile integrity and pressure in the system. When the trigger is engaged, the fiber optic waveguide can be instantly extracted from the needle with minimal motion of the needle tip.

Figure 2:
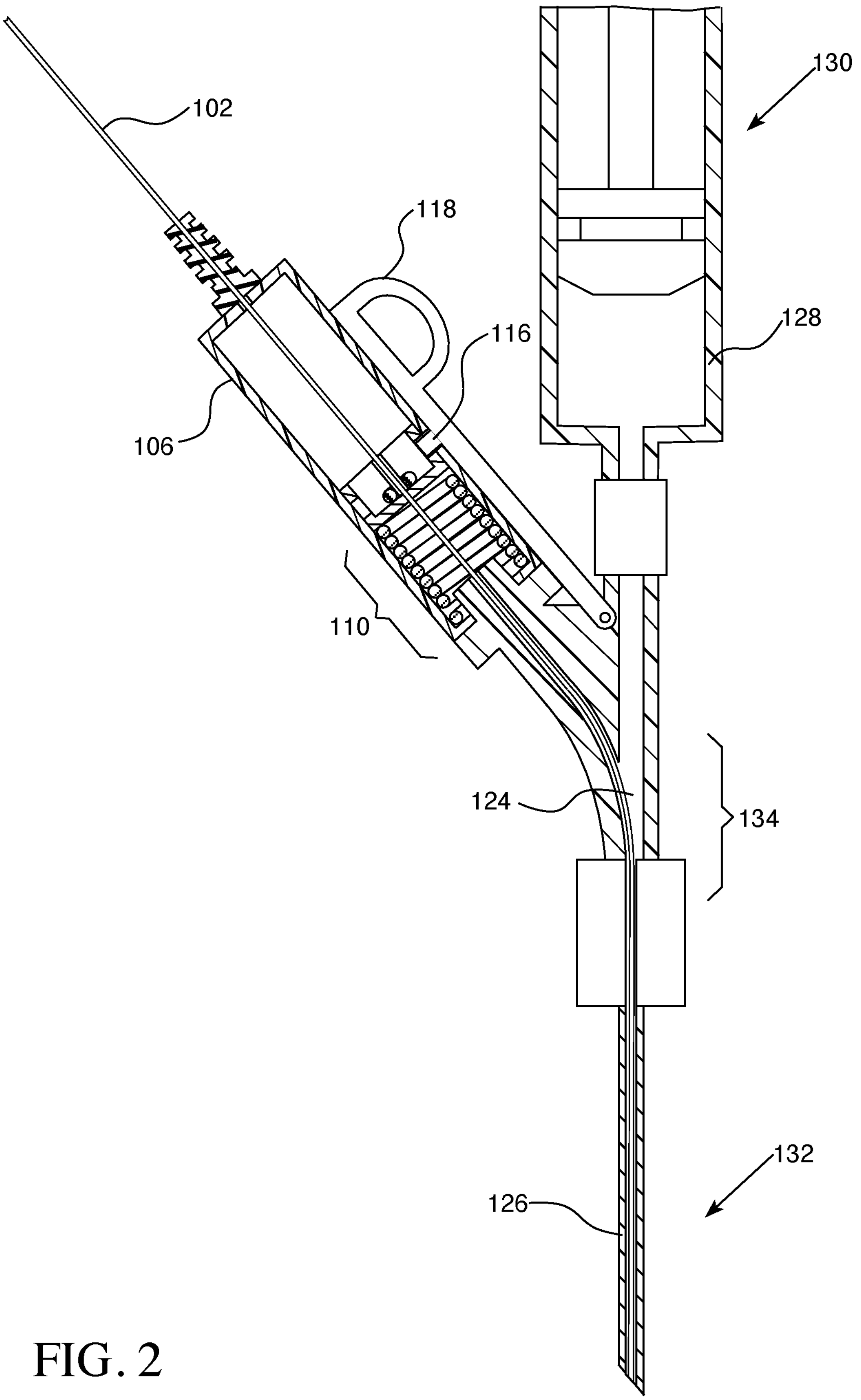
FIG. 2 is an illustrative example of another embodiment of a retraction system according to the present disclosure.

In FIG. 1, fiber optic sensor retraction system 100 may having a bifurcated configuration. In one embodiment, fiber optic sensor retraction system 100 may have a distal end 132 and a proximal end 130. Distal end 132 may include a hollow needle 126 for administering medical fluids. Needle 126 can be in fluid communication to a fluid channel 124. A fiber optic waveguide, such as optical fiber 102, may extend from hollow needle 126 and through fluid channel 124 into a spring housing (or spring barrel) 106. Spring barrel 106 may be located on proximal end 130 and spring barrel 106 may include a spring 110. Spring 110 can be at least one of a helical coil, solenoid based, disc, Belleville washer, wave spring or any combination thereof. In one configuration of one embodiment, spring 110 can be compressed down into spring barrel 106. To maintain the compressed state, a retraction trigger 118 can be in a closed position, extending a retraction flange or pin 116 into an opening or slot 140 of spring barrel 106. Retraction pin 116 may engage or contact at least a part of spring 110, holding spring 110 in a first compressed position, as illustrated in FIG. 2. In another embodiment, retraction pin 116 may engage or contact another part, such as a retraction socket 108, which can be located on one end of spring 110 such that when retraction pin 116 engages with retraction socket 108, then retraction pin 116 retains spring 110 in a compressed position. Optical fiber 102 may continue from fluid channel 124 and extend through spring barrel 106 and spring 110. In some embodiments, a seal 112 may be present at the distal end of spring barrel 106 (i.e., the end nearest fluid channel 124) or at the entrance of fluid channel 124 into spring barrel 106 for preventing fluid from entering spring barrel 106.

As mentioned above, another part of fiber optic sensor retraction system 100 can be a branching of fluid channel 124 into a Y-junction configuration. Hollow needle 126 may be an output arm 134 connecting to a bifurcation of fluid channel 124 into two parts: a first arm 136 with, or connecting to, spring barrel 106 as described herein, and a second arm 138 at proximal end 130. Second arm 138 may connect to a lure lock 128 as in FIG. 1 that is configured to connect with a syringe (not pictured). Lure lock 128 may have a seal 114, limiting contaminants and fluid leakage from fluid channel 124 from getting into spring barrel 106. Seal 114 may be broken when a syringe is connected to lure lock 128 at proximal end 130 at the opening that seals fluid channel 124 when not engaged. The seal 114 may be present at the opening or on lure lock 128 to keep the fluid channel closed from air and contaminants until a syringe (not pictured) is engaged or seal 114 is broken.

When fiber optic sensor retraction system 100 is in a first position, as illustrated in FIG. 2, retraction pin 116 can be engaged in opening 140 of spring barrel 106 (such as retraction pin 116 engaged in spring barrel 106 of FIG. 2), thereby compressing retraction spring 110. In this first position, optical fiber 102 can extend through spring 110 and into fluid channel 124 through first arm 136, continuing through output arm 134 and through hollow needle 126. Because optic fiber 102 can extend out to an opening of hollow needle 126, certain compounds and elements that hollow needle 126 comes into contact with may be detected by the tip of optical fiber 102. In one embodiment, a doctor or dentist may need to deliver fluid such as medicine to an area of the patient's mouth or spine, as well as any other medical procedure locations of the patient's body. The medicine may need to be delivered to the target tissue to prevent unwanted side effects by avoiding delivery of the medicine into undesired locations, such as, but not limited to, the vascular system.

The bifurcated configuration may allow for delivery of medicine in the target location while avoiding improper delivery areas of the patient. When used, a physician or health care professional may connect a syringe of fluid to lure lock 128 on second arm 138, before or after hollow needle 126 is placed into tissue of the patient. Optical fiber 102 may use light to detect the present of biomarkers, such as blood or other biological elements in a biological system. Detection of such biomarkers may help the physician or clinician to determine that hollow needle 126 was placed in the wrong location. In one embodiment, an illumination diode (not pictured in FIG. 1) may be at, or near, the tip or opening of hollow needle 126, and can shine light along optical fiber 102. In this way, the optical system can deliver light to a material to help the user detect or identify blood. The material can be a biomarker luminescent material (for example, luminescent material, fluorescent material, phosphorescent material, chemiluminescent material, or combinations thereof), which is a material that may react with the iron ions from a patient's blood and produce light. This production of light can be part of the identification process of the location of the needle (i.e., determining whether the needle tip is in the bloodstream), and the light produced and emitted by the reaction can be further amplified by the illumination diode and simultaneously transmitted from the location of the biomarker luminescent material to a detector in the optical system. The detector (not illustrated in FIG. 1) may connect to or be part of a circuit board that includes one or more wireless interfaces.

Such a diode may be a waveguide or waveguide sensor, which can detect light. In this case, the diode can detect the light produced by the reaction between iron ions from a patient's blood and the biomarker luminescent material. Hollow needle 126 may have sensing, such as with a waveguide sensor, at the opening of the needle tip, and the electrons present in the luminescent, fluorescent, phosphorescent, or chemiluminescence material may be excited to a higher state when put into contact with the biological tissue (for example, blood). More specifically, if, during the insertion of the needle into tissue, blood is released from a patient's blood vessel and the iron ions from the blood comes into contact with the electrons from the biomarker luminescent material, the electrons may become excited, photons may be emitted, and a visual signal may be generated based on the reaction between the iron ions and the biomarker luminescent material. In other embodiments, ions or photons may react to be in a higher, energized state.

In one embodiment, fluorescence can be on the tip of optical fiber 102 and can react with iron ions and, optionally, added light through optical fiber 102. The light produced by the reaction between the blood and the iron-ion detecting substrate may be transmitted toward the needle opening. More specifically, the emitted light from the reaction of the biomarker luminescent material to the iron ions may cause light to travel back through optical fiber 102 and into a computing device that detects light. In some embodiments, optical fiber 102 may add light as well. In one such way, fiber optic sensor retraction system 100 can deliver light to biomarker luminescent material and simultaneously transmit emitted light from the biomarker luminescent material to a detector, such as a computing device connected to optical fiber 102 for receiving light and signals. The generated visual signal may be a result of the luminescent, fluorescent, phosphorescent, or chemiluminescent light produced by the interaction between blood and the iron-ion detecting substrate as described above.

In one embodiment, the light emitted along optical fiber 102 is blue light, and contacting iron from the biomarker, such as blood, may cause emitted photons, which can be green light. The green light can be sent into a splitter, and half of the green light can go to a detector that measures luminosity. In one embodiment, Photo Darlington detector, or a similar type, may convert light intensity to voltage level. In one embodiment, the output may be a voltage reading related to the biomarker concentration at the tip of hollow needle 126. The voltage reading may be visible to the user to determine placement of the needle in the patient. When the voltage reaches a certain level or passes a threshold, then a notification may be given to alert the clinician of the presence of a certain biomarker material.

Coating thicknesses and permeability of the different layers of the biomarker luminescent material can be adjusted to modify the ion sensing response time. In some embodiments, coating compositions are substantially transparent to the light wavelength emitted by the florescent coating so that emitted light can enter the fiber optic wave guide or selected optical transmission medium. Another contemplated embodiment can incorporate nanoparticles in the fluorescence coating itself, wherein the fluorescent media coating can slowly release chemicals to consume the iron ions over time, but not so fast as to inhibit the florescent coating from illuminating in the presence of the target ion.

In one embodiment, fiber optic sensor retraction system 100 further has an optical receiver (not illustrated) having a filter to selectively prevent frequencies, other than the frequency of emitted light from the biomarker luminescent material, from reaching the optical receiver. Therefore, in this embodiment, the physician or health care professional may not receive any alerts or notifications until a predetermined frequency of emitted light is detected by the system.

In one embodiment, once a desired placement of hollow needle 126 has occurred, then the medicine may be delivered. The user may cause optical fiber 102 to vacate fluid channel 124 by moving on retraction trigger 118. Retraction trigger 118 may be pulled, releasing retraction pin 116 from opening 140 of spring barrel 106. Because retraction pin 116 can directly or indirectly hold spring 110 in a first compressed position, as illustrated in FIG. 2, then the removal of pin 116 allows the force of spring 110 to retract into an expanded second position, as illustrated in FIG. 1. Optical fiber 102 may, in some embodiments, connect or mechanically connect to at least one of spring 110, retraction socket 108, or a combination, causing optical fiber 102 to move in the retracting direction of spring 110, which may be away from distal end 132 and towards proximal end 130. In the embodiment of FIG. 1, retraction of spring 110 may move optical fiber 102 from fluid channel 124 of output arm 134 distally through first arm 136, vacating output arm 134. In this embodiment, vacating fluid channel 124 of output arm 134 may allow for fluid to fill fluid channel 124 since optical fiber 102 is no longer blocking fluid channel 124. However, in some embodiments, when optical fiber 102 does not fill the space of fluid channel 124, fluid may fill fluid channel 124 even when optical fiber 102 is present in output arm 134.

As illustrated in FIG. 1, spring 110 is in a second position that is a retracted spring position with the optical fiber 102 not present in fluid channel 124, so when a syringe (not illustrated) is connected and delivers fluid through fluid channel 124, the fluid may flow to hollow needle 126 from second arm 138 to output arm 134. In some embodiments, retraction socket 108 may have a connection area where optical fiber 102 extends through, and a connector 104, such as an O-ring, washer, seal, or other part that holds spring 110 in mechanical communication with retraction socket 108.

Once optical fiber 102 is retracted, then sensing of biomarkers may cease. In some embodiments, the optical fiber waveguide may sense the presence of biological material by using sensors. Therefore, when optical fiber 102 is retracted into the second position, such as in FIG. 1, then certain light emitted when ion and other biomarkers are present, such as when blood is present at hollow needle 126 sensor, may no longer sense that biomarkers are present.

FIG. 2 is an embodiment of the first position before a spring 110 is retracted. This illustration is an embodiment of the original, first, position before retraction trigger 118 is pulled away from slot 140 of spring barrel 106. In the illustration, retraction trigger 118 is locked in place and pin 116 is engaging slot 140 of spring barrel 106. Pin 116 engages spring 110 by holding it in a compressed position, which is the first position and illustrated in FIG. 2. Spring 110 can be held retracted by pin 116 in moveable communication.

Optical fiber 102 may be a waveguide, which may moveably or slidably fit within the lumen of fluid channel 124 and may further have an optical coupler. The slide-ability of optical fiber 102 retracting out of fluid channel 124 may be due to a cylinder outside of optical fiber 102. More specifically, because optical fiber 102 may have a smaller diameter than a cylinder or cylindrical housing, such as spring barrel 106, optical fiber 102 may slide within the cylinder, or spring barrel 106. Optical fiber 102 of FIG. 2 is in the first position with spring 110 compressed, with pin 116 engaged in slot 140 of spring barrel 106. Thus, in this first position, optical fiber 102 can be in the fluid channel 124 of output arm 134. This placement can continue until pin 116 is removed from slot 140, causing spring 110 to recoil, and the spring expansion to move optical fiber 102 out of output arm 134, vacating fluid channel 124.

Figure 3:
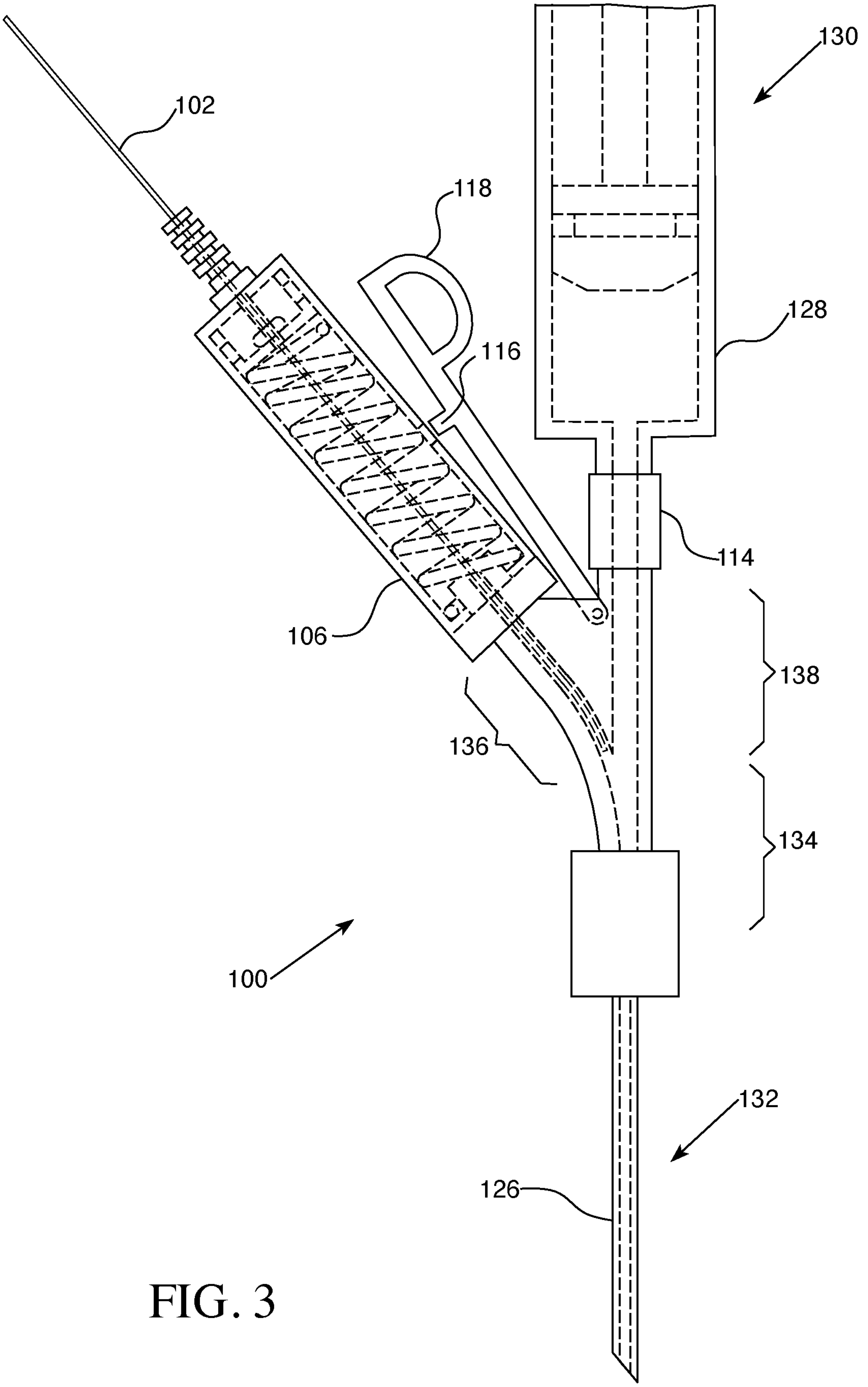
FIG. 3 is an illustrative example of an exterior view of a retraction system according to the present disclosure.

Other embodiments of the fiber optic sensor retraction system may use other retraction methods that do not require a spring for retraction, such as hydraulics. For example, as the plunger of the syringe is depressed, the pressure of the syringe can be felt equally by the fiber optic waveguide/optical fiber and a fiber optic extraction cylinder, which can be used in place of the spring barrel that is illustrated in FIGS. 1-3. In this embodiment, the surface area of the extraction cylinder can be much larger than the fiber optic waveguide/optical fiber. The movement of the plunger may be interconnected with the fiber optic waveguide/optical fiber, such that when pressure is applied to the plunger, such as fluid pressure, then the fiber optic waveguide/optical fiber can be retracted out of the fluid channel of the needle. The waveguide can be smoothly and easily extracted by the extraction cylinder allowing for the fluid in the syringe to be ejected out from the syringe and into the needle. Other methods for moving the optical fiber out of the fluid channel are within the scope of this disclosure.

FIG. 3 is an illustration of the outside of the disclosed system and device as described herein. The dotted lines represent the inner elements as described herein. The solid lines represent the exterior of the device and system.

Persons of ordinary skill in arts relevant to this disclosure and subject matter hereof will recognize that embodiments may comprise fewer features than illustrated in any individual embodiment described by example or otherwise contemplated herein. Embodiments described herein are not meant to be an exhaustive presentation of ways in which various features may be combined and/or arranged. Accordingly, the embodiments are not mutually exclusive combinations of features; rather, embodiments can comprise a combination of different individual features selected from different individual embodiments, as understood by persons of ordinary skill in the relevant arts. Moreover, elements described with respect to one embodiment can be implemented in other embodiments even when not described in such embodiments unless otherwise noted. Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless stated that a specific combination is not intended. Furthermore, it is also intended to include features of a claim in any other independent claim, even if this claim is not directly made dependent on the independent claim.

The invention claimed is:

1. A fiber optic sensor retraction system comprising:
- a retraction system having a distal end and a proximal end;
- a hollow needle located at the distal end of the retraction system;
- an opening at the proximal end of the retraction system configured to receive medical fluids through a fluid channel,
- a spring housing connected between the distal and proximal ends of the retraction system;
- a spring disposed within the spring housing that is in mechanical communication with a fiber optic waveguide, and wherein the spring has a compressed position and an expanded position;
- an optical system, wherein the optical system comprises the fiber optic waveguide that is at least partially contained within the hollow needle, when the spring is in the compressed position, and extends through a Y-junction, and wherein the fiber optic waveguide is configured to allow entry of an emitted light from a biomarker luminescent material at a bevel of the hollow needle;
- a notification system in communication with the optical system, wherein the notification system is configured to inform a clinician of a detected biomarker; and
- a syringe configured to contain the medical fluids, wherein the syringe is in fluid communication with the Y-junction.

2. The fiber optic sensor retraction system according to claim 1, wherein the spring is a retraction spring, the hollow needle is in fluid communication with the Y-junction, and the fluid channel is comprised of a first input arm, a second input arm, and an output arm, wherein the spring housing is connected to the first input arm.

3. The fiber optic sensor retraction system according to claim 2, wherein the fiber optic waveguide is located within a lumen of the fluid channel and further comprises at least an optical fiber, an optical coupler, or both.

4. The fiber optic sensor retraction system according to claim 1, further comprising a retraction trigger disposed on the spring housing and in mechanical communication with the spring.

5. The fiber optic sensor retraction system according to claim 1, further comprising the medical fluid within the syringe, wherein the syringe is configured to deliver the medical fluid through the fluid channel to a biological system.

6. The fiber optic sensor retraction system according to claim 1, wherein the optical system is configured to simultaneously deliver light to the biomarker luminescent material and transmits the emitted light from the biomarker luminescent material.

7. The fiber optic sensor retraction system according to claim 1, wherein the proximal end comprises a Luer lock configured to receive the syringe.

8. The fiber optic sensor retraction system according to claim 1, wherein the optical system further comprises an optical receiver having a filter configured to allow a predetermined frequency of the emitted light to be detected.

9. The fiber optic sensor retraction system according to claim 1, wherein the retraction system, when configured with the spring in the compressed position, has the optical fiber located within a lumen of an output arm of the Y-junction, and when configured with the spring in the expanded position, allows the medical fluids to flow through the fluid channel and into the hollow needle.

10. The fiber optic sensor retraction system according to claim 1, wherein the spring is at least one of a helical coil, solenoid based, disc, Belleville washer, wave spring or any combination thereof.

11. The fiber optic sensor retraction system according to claim 1, wherein a spring recoil rate is preselected based on a spring tension.

12. The fiber optic sensor retraction system according to claim 1, wherein the proximal end of the retraction system contains a Luer lock configured to connect with the syringe.

13. The fiber optic sensor retraction system according to claim 1, further comprises a barrel connected to the optical fiber, wherein the optical fiber has a smaller diameter than the barrel.

14. The fiber optic sensor retraction system according to claim 1, wherein the spring housing is configured to house the spring and at least a portion of the optical fiber.

15. The fiber optic sensor retraction system according to claim 1, wherein a pin holds the spring in the compressed position.

16. A fiber optic sensor retraction system comprising:

a retraction system having a distal end and a proximal end;

a hollow needle located at the distal end of the retraction system;

an opening at the proximal end of the retraction system configured to receive medical fluids through a fluid channel, a spring housing connected between the distal and proximal ends of the retraction system;

a spring disposed within the spring housing that is in mechanical communication with a fiber optic waveguide, and wherein the spring has a compressed position and an expanded position;

an optical system, wherein the optical system comprises the fiber optic waveguide that is at least partially contained within the hollow needle, when the spring is in the compressed position, and extends through a Y-junction, and wherein the fiber optic waveguide is configured to allow entry of an emitted light from a biomarker luminescent material at a bevel of the hollow needle;

wherein the optical system is configured to send optical signals from the needle through the fiber optic waveguide; and a syringe configured to contain the medical fluids, wherein the syringe is in fluid communication with the Y-junction.

17. A fiber optic sensor retraction system comprising:

a retraction system having a distal end and a proximal end;

a hollow needle located at the distal end of the retraction system;

an opening at the proximal end of the retraction system configured to receive medical fluids through a fluid channel, a spring housing connected between the distal and proximal ends of the retraction system;

a spring disposed within the spring housing that is in mechanical communication with a fiber optic waveguide, and wherein the spring has a compressed position and an expanded position;

an optical system, wherein the optical system comprises the fiber optic waveguide that is at least partially contained within the hollow needle, when the spring is in the compressed position, and extends through a Y-junction, and wherein the fiber optic waveguide is configured to allow entry of an emitted light from a biomarker luminescent material at a bevel of the hollow needle;

a detector having a circuit board that includes one or more wireless interfaces; and a syringe configured to contain the medical fluids, wherein the syringe is in fluid communication with the Y-junction.

* * * * *